(12) United States Patent
Andresen

(10) Patent No.: US 10,070,941 B2
(45) Date of Patent: Sep. 11, 2018

(54) THIN-FORM NIGHTGUARD

(71) Applicant: Nord Andresen, Berkeley, CA (US)

(72) Inventor: Nord Andresen, Berkeley, CA (US)

(73) Assignee: NORDIC DESIGN, LLC, Berkeley, CA (US)

( * ) Notice: Subject to any disclaimer, the term of this patent is extended or adjusted under 35 U.S.C. 154(b) by 513 days.

(21) Appl. No.: 14/719,181

(22) Filed: May 21, 2015

(65) Prior Publication Data

US 2016/0338800 A1   Nov. 24, 2016

(51) Int. Cl.
*A61F 5/56* (2006.01)
*A61C 7/08* (2006.01)
*A63B 71/08* (2006.01)

(52) U.S. Cl.
CPC .............. *A61C 7/08* (2013.01); *A63B 71/085* (2013.01); *A61C 2202/00* (2013.01); *A61F 2005/563* (2013.01)

(58) Field of Classification Search
CPC . A61C 7/08; A61C 2202/00; A61F 2005/563; A63B 71/085
See application file for complete search history.

(56) References Cited

U.S. PATENT DOCUMENTS

| | | | |
|---|---|---|---|
| 1,910,740 A * | 5/1933 | Barsha | A61C 9/00 433/159 |
| 4,063,552 A * | 12/1977 | Going | A63B 71/085 128/861 |
| 5,103,838 A | 4/1992 | Yousif | |
| 5,746,221 A * | 5/1998 | Jones | A63B 71/085 128/859 |
| 6,089,864 A | 7/2000 | Hintermister et al. | |
| 7,024,770 B2 | 4/2006 | Sun et al. | |
| 2008/0138755 A1* | 6/2008 | Jansheski | A61F 5/566 433/6 |
| 2009/0038624 A1 | 2/2009 | Akervall et al. | |
| 2009/0202958 A1 | 8/2009 | Knutson | |
| 2010/0044895 A1 | 2/2010 | Sun et al. | |
| 2014/0060549 A1 | 3/2014 | Lucas | |
| 2014/0238415 A1 | 8/2014 | Lucas | |
| 2014/0338675 A1 | 11/2014 | Akervall et al. | |

FOREIGN PATENT DOCUMENTS

WO   WO 2014/199370   12/2014

OTHER PUBLICATIONS

International Search Reported dated Jul. 27, 2016 in International Application No. PCT/US2016/033121.

* cited by examiner

*Primary Examiner* — Matthew J Daniels
*Assistant Examiner* — Kelsey C Grace
(74) *Attorney, Agent, or Firm* — Knobbe, Martens, Olson & Bear, LLP

(57) ABSTRACT

A thin-form mouthguard can be formed from a U-shape planar sheet. The sheet can be made of expanded-polytetrafluoroethylene and have a thickness between 0.02 inches and 0.25 inches. The sheet can also include instructions for modification of the mouthguard printed thereon. A method for preparing a mouthguard is also provided.

20 Claims, 4 Drawing Sheets

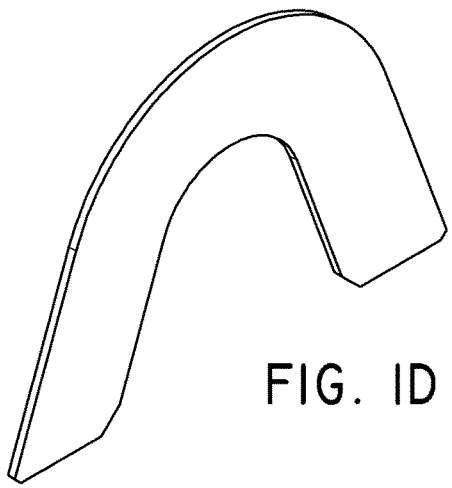
FIG. ID
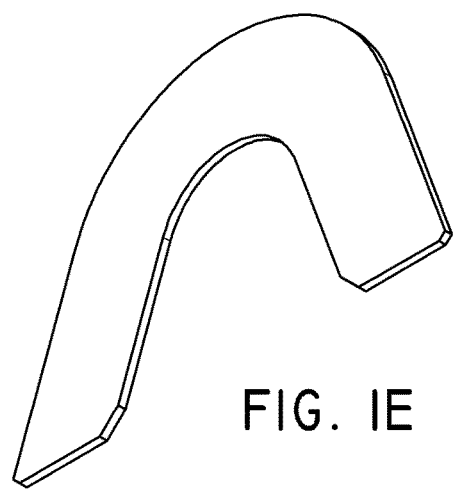
FIG. IE

THIN-FORM NIGHTGUARD

BACKGROUND OF THE INVENTIONS

Field of the Inventions

The application relates to devices for protecting a person's teeth, such as mouthguards.

Description of the Related Art

Various devices exist for protecting a person's teeth from various forms of trauma such as grinding (for example, bruxism) and sudden impact. Some mouthguards are prefabricated to fit the unique contours of an individual's teeth. However, these require a mold to be created, time for the custom piece to subsequently be made, and significant expense.

Other mouthguards include a thermoplastic material that can be heated to a predetermined temperature, at which point the mouthguard is bitten by the user and deforms to match the user's teeth. These mouthguards require a large amount of material to mold around the user's teeth. The large size can be uncomfortable and block saliva flow to teeth.

SUMMARY OF THE INVENTIONS

In one embodiment, a method for preparing a mouthguard from a U-shaped planar sheet is provided. The sheet can be trimmed to a size that fits between a user's cheeks and over the user's teeth. The user can then bite on the sheet to create an imprint of the user's teeth on the sheet. The sheet can then be further trimmed around the imprint to create a mouthguard having a size and shape substantially matching a user's bite pattern.

In a further embodiment, a thin-form mouthguard can be formed from a U-shape planar sheet. The sheet can be made of expanded-polytetrafluoroethylene and have a thickness between 0.02 inches and 0.25 inches. The sheet can also include instructions for modification of the mouthguard printed thereon.

In a further embodiment, a mouthguard package can include a thin-form mouthguard and instructions for modification of the mouthguard. The mouthguard can be made from a U-shape planar sheet made of expanded-polytetrafluoroethylene and have a thickness between 0.02 inches and 0.25 inches. The instructions can instruct the user to trim the sheet to a size that fits between a user's cheeks and over a user's teeth. The instructions can then say to bite on the sheet to create an imprint of the user's teeth on the sheet. The instructions can also say to trim the sheet around the imprint to create a mouthguard having a size and shape substantially matching the user's bite pattern.

In a further embodiment, a thin-form mouthguard can be made of a U-shape planar sheet. The sheet can be made of expanded-polytetrafluoroethylene and have a thickness between 0.02 inches and 0.25 inches.

BRIEF DESCRIPTION OF THE DRAWINGS

These and other features, aspects, and advantages of the invention disclosed herein are described below with reference to the drawings of embodiments, which are intended to illustrate and not to limit the invention. Additionally, from figure to figure, the same reference numerals have been used to designate the same components of an illustrated embodiment. The following is a brief description of each of the drawings.

FIGS. 1D and 1E depict perspective views of the mouthguard of FIG. 1.

DETAILED DESCRIPTION

Figure 1:
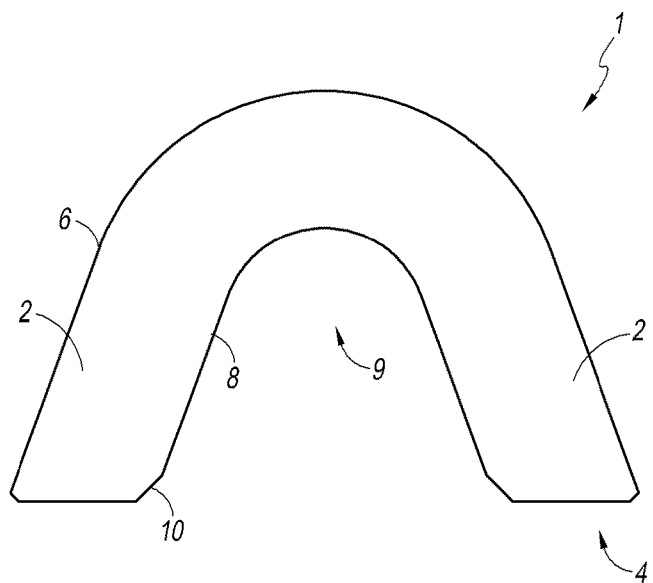
FIG. 1 depicts a top view of an embodiment mouthguard before initial use.
Figure 1A:
FIG. 1A depicts a side view of the mouthguard of FIG. 1.
Figure 1B:
FIG. 1B depicts a front view of the mouthguard of FIG. 1.
Figure 1C:
FIG. 1C depicts a back view of the mouthguard of FIG. 1.

FIG. 1 depicts an embodiment mouthguard 1 before initial use. As shown, the mouthguard 1 can be substantially planar with a U-shape having two elongated arms 2 configured to substantially match a user's mouth. The U-shape can form a gap 9 formed by inner edges 8 of the mouthguard 1, such that a roof or floor of a user's mouth is not occluded by the mouthguard. Further, the corners of the inner edges 8, at the ends 4 of the U-shape can include a chamfer or rounding 10, for reducing the chance of contacting the posterior pharyngeal wall and inducing a pharyngeal reflex response (such as a gag reflex). Chamfers and roundings can also be provided on the corners of the exterior edges 6 at the ends 4 of the U-shape.

Variations on this shape are also possible. For example, in some embodiments the bevels can be rounded instead of being formed by a single angled cut, multiple angled cuts, or can optionally not have any chamfer or rounding. Further, the mouthguard 1 can have a gap 9 between the arms of the U-shape. As discussed further below, the user can optionally create this gap by trimming the mouthguard 1 to fit the particular shape of the user's bite.

Further, the mouthguard 1 can have varying thicknesses in some embodiments, such as having a greater thickness in a central region where the user would bite, and a lesser thickness along the perimeter of the mouthguard, near the exterior edges 6. The mouthguard 1 can also optionally have splayed portions at the exterior edges 6, configured to wrap over the sides of a user's teeth. In some embodiments, the mouthguard 1 can be configured to tear at these splayed portions such that the beginning of the splay can be adjusted to begin at the position of a user's teeth on the mouthguard.

The mouthguard 1 can be sized and shaped to match an individual user's mouth. Additionally, the mouthguard 1 can optionally have a thickness between 0.02 inches and 0.25 inches, although other thicknesses are also possible.

The mouthguard 1 can be formed from a resilient material that can mold to the shape of a user's teeth. In some embodiments, this can be done without needing to heat the mouthguard 1 to a particular temperature. Further, the material can have a substantially long lifetime, such that it can be used for at least multiple months of normal use by a user with bruxism. Further, the material can be easy to cut or trim with household scissors.

In some embodiments, the mouthguard 1 can be a piece of polytetrafluoroethylene ("PTFE"). Even further, the mouthguard 1 can be a piece of expanded-PTFE ("ePTFE"). Other types of PTFE, other polymers (such as other fluoropolymers), and other materials can also be used to form the mouthguard. For example, in some embodiments the mouthguard 1 can be formed partially from ePTFE, but also partially from another material. The ePTFE, for example, can be used in a central region of the mouthguard 1, positioned to receive substantial physical stress from the teeth, while other materials can be used on the perimeter of the mouthguard to promote: self-alignment of the mouthguard with the sides of the teeth, flow of saliva to and from the teeth, comfort, and other benefits. It is also possible for the mouthguard 1 to include ePTFE as an exterior of the mouthguard with a less pliable material within the ePTFE layer. In some embodiments, the perimeter material can include small holes or an otherwise more porous material configured to promote saliva flow without significantly impeding self-alignment with the teeth.

Figure 3:
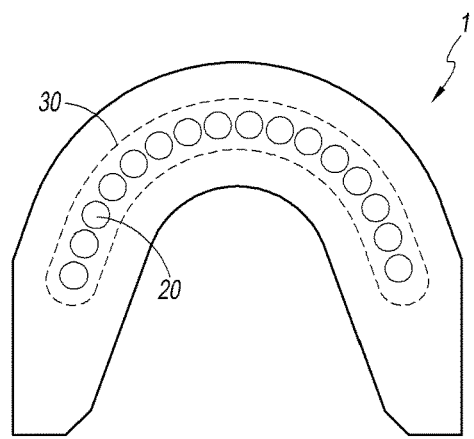
FIG. 3 depicts a top view of the mouthguard of FIG. 2 after modification and use, but before further modification.

A user can bite onto the mouthguard 1, and the material can then mold to fit a user's teeth. The precise fit can then cause the mouthguard 1 to reliably self-align and stick to the user's teeth until the user desires to remove it. Advantageously, the bite marks can also indicate to a user the previous position of their teeth on the mouthguard 1 before it has been removed, as shown in FIG. 3. The mouthguard 1 can then be modified to better fit the user.

Figure 2:
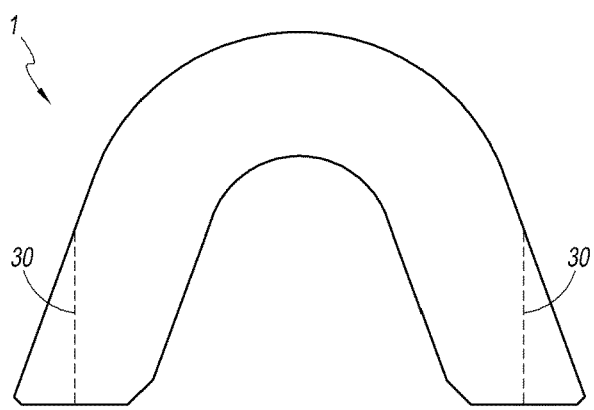
FIG. 2 depicts a top view of the mouthguard of FIG. 1 before modification.

For example, the user can initially place the mouthguard 1 in their mouth to verify that the width of the outer edges of the mouthguard fits within the user's cheeks. If the mouthguard 1 is wider than the user's cheeks, the user can trim the outer edges of the mouthguard to fit between the user's cheeks with scissors or other cutting tools, as indicated in FIG. 2, showing cut lines 30.

Figure 4:
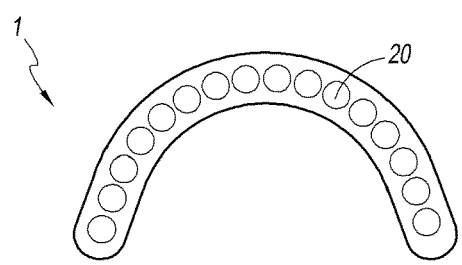
FIG. 4 depicts a top view of the mouthguard of FIG. 3 after further modification.

When the mouthguard 1 is sized to fit within a user's mouth and cover the teeth, the user can fully insert it and bite on it once to create an imprint 20 matching the user's bite pattern, as shown in FIG. 3. The user can then remove the mouthguard 1 and trim it further to better fit the teeth and mouth, as indicated in FIGS. 3 and 4 showing a mouthguard before and after trimming. For example, the user can trim the mouthguard 1 at the ends 4 of the U-shape to fit the back of their bite imprint 20. Further, the user can trim the mouthguard 1 around its perimeter to remove excess material. A user can, for example, trim the mouthguard 1 leaving approximately ⅛ inch between the bite-imprint 20 and the edge of the mouthguard. The mouthguard 1 can deform under pressure during biting by the user, such that it conforms to the user's teeth and remains aligned with the user's teeth. Thus, the user can sleep at night without it falling out. Further, the ability to easily trim the material with household scissors allows a user to remove excess material, improving comfort.

Figure 5:
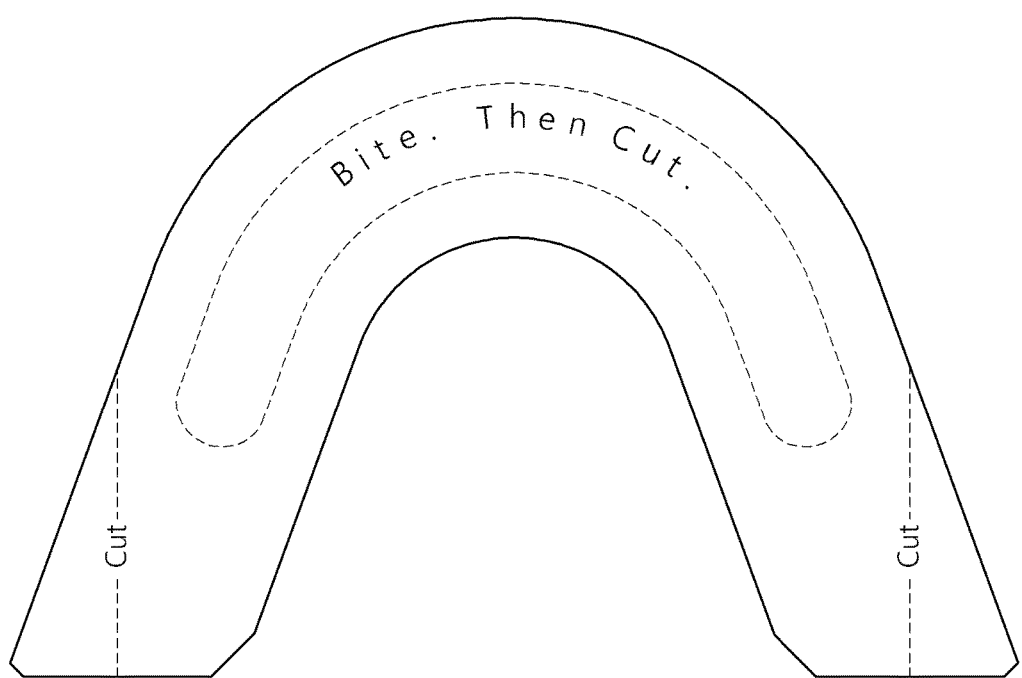
FIG. 5 depicts a top view of an embodiment mouthguard, including instructions for modification.

In some embodiments, the mouthguard 1 can be provided in a package including instructions for modifying and using the mouthguard in any way discussed herein. Even further, in some embodiments the mouthguard 1 can include instructions imprinted directly on the mouthguard, as shown in FIG. 5. The mouthguard 1 can include suggested lines printed on the mouthguard, along which one can trim to accommodate cheek width, such as dotted or dashed lines on either side of the U-shape to extend along a length of the each arm of the U-shape. The mouthguard 1 can also include suggested lines along which one can trim to fit their bite imprint. For example, the mouthguard 1 could include a printed inner-perimeter with tooth outlines inside it, indicating where one would cut if their teeth imprints were in that position.

Further, the mouthguard 1 can be used to aid dental care. For example, the mouthguard 1 can show contact patterns according to the pressure exerted by the user's bite in the imprints 20. In areas where the biting is particularly strong, the mouthguard 1 can gradually become translucent, indicating where the biting force is strong. This can be used, for example by a dental professional, to determine how to provide or modify existing dental implants such as fillings and crowns. Bruxism is known to cause these implants and their underlying teeth to be damaged under strong biting pressure. Thus, knowledge of the pattern of wear can indicate points of high pressure where such implants should be avoided or corrected. Further, in some embodiments subsequent mouthguards can be made thicker in areas indicated to have high biting forces, such that subsequent mouthguards can have a longer lifetime. A user can be instructed to send a worn-mouthguard to a mouthguard provider, and the provider can user that mouthguard to determine an ideal thickness profile for that user's subsequent mouthguards, and can further pre-shape the mouthguard to be substantially pre-trimmed to fit the user's mouth.

While not being used, the mouthguard 1 can be stored in a container. In some embodiments, the mouthguard can be kept in a storage wallet that facilitates travel and transport. Further, in some embodiments the storage wallet can be configured to hold a disinfectant such as 3% hydrogen peroxide to immerse the mouthguard 1 and clean it for future use.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others. Additionally, features described in connection with one embodiment can be incorporated into another of the disclosed embodiments, even if not expressly discussed herein, and the prosthetic device having the combination of features still fall within the scope of the invention. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method for preparing a nightguard from a U-shaped planar sheet comprising the steps of:
    trimming the planar sheet to a size that fits between a user's cheeks and over the user's teeth;
    biting on the planar sheet to create an imprint of the user's teeth on the sheet;
    after biting on the planar sheet, trimming the sheet around the entire perimeter of the imprint to create a nightguard having a size and shape substantially matching a user's bite pattern; and
    biting the nightguard after trimming around the perimeter.

2. The method of claim 1, wherein the nightguard is trimmed with scissors.

3. The method of claim 1, further comprising the step of using the nightguard for determining where dental implants are appropriate for the user.

4. The method of claim 1, further comprising the step of biting the nightguard a plurality of times.

5. The method of claim 4, further comprising the step of providing the nightguard to a dental professional after the step of biting the nightguard a plurality of times.

6. The method of claim 1, further comprising the step of sleeping with the nightguard inserted in the user's mouth.

7. The method of claim 1, the sheet consisting essentially of expanded-polytetrafluoroethylene and having a thickness between 0.02 inches and 0.25 inches.

8. The method of claim 6, further comprising the step of providing the nightguard to a dental professional after the sleeping with the nightguard inserted in the user's mouth.

9. The method of claim 1, further comprising the step of manually inserting the sheet into a user's mouth.

10. A method for preparing a night guard from a U-shaped planar sheet comprising the steps of:
    trimming the planar sheet to a size that fits between a user's cheeks and over the user's teeth;
    manually inserting the sheet into a user's mouth;
    biting on the sheet to create an imprint of the user's teeth on the sheet; and
    trimming the sheet around the imprint to create a nightguard having a size and shape substantially matching a user's bite pattern,
    wherein the sheet consists essentially of expanded-polytetrafluoroethylene.

11. The method of claim 10, wherein the nightguard is trimmed with scissors.

12. The method of claim 10, further comprising the step of using the nightguard for determining where dental implants are appropriate for the user.

13. The method of claim 10, further comprising the step of biting the nightguard a plurality of times.

14. The method of claim 13, further comprising the step of providing the nightguard to a dental professional after the step of biting the nightguard a plurality of times.

15. The method of claim 10, further comprising the step of sleeping with the nightguard inserted in the user's mouth.

16. The method of claim 15, further comprising the step of providing the nightguard to a dental professional after the sleeping with the nightguard inserted in the user's mouth.

17. The method of claim 10, wherein the sheet has a thickness between 0.02 inches and 0.25 inches.

18. A method for preparing a nightguard from a U-shaped planar sheet comprising the steps of:
    manually inserting the sheet into a user's mouth;
    biting on the sheet to create an imprint of the user's teeth on the sheet; and
    trimming the sheet around the entire perimeter of the imprint to create a nightguard having a size and shape substantially matching a user's bite pattern; and
    sleeping with the nightguard inserted in the user's mouth.

19. The method of claim 18, wherein the sheet consisting essentially of expanded-polytetrafluoroethylene and having a thickness between 0.02 inches and 0.25 inches.

20. The method of claim 18, further comprising the step of biting the nightguard a plurality of times.

* * * * *